(12) United States Patent
Sugiyama

(10) Patent No.: US 8,735,357 B2
(45) Date of Patent: May 27, 2014

(54) METHOD OF INDUCING ANTIGEN-SPECIFIC T CELLS

(75) Inventor: Haruo Sugiyama, Minoo (JP)

(73) Assignee: International Institute of Cancer Immunology, Inc., Suita-shi (JP)

( * ) Notice: Subject to any disclaimer, the term of this patent is extended or adjusted under 35 U.S.C. 154(b) by 1346 days.

(21) Appl. No.: 10/490,873

(22) PCT Filed: Sep. 27, 2002

(86) PCT No.: PCT/JP02/09993
§ 371 (c)(1),
(2), (4) Date: Jun. 17, 2004

(87) PCT Pub. No.: WO03/028757
PCT Pub. Date: Apr. 10, 2003

(65) Prior Publication Data
US 2004/0247609 A1 Dec. 9, 2004

(30) Foreign Application Priority Data

Sep. 28, 2001 (JP) ................. 2001-301206

(51) Int. Cl.
*A61K 38/00* (2006.01)
(52) U.S. Cl.
USPC ......................... 514/19.3; 514/21.6
(58) Field of Classification Search
None
See application file for complete search history.

(56) References Cited

U.S. PATENT DOCUMENTS

| | | | |
|---|---|---|---|
| 4,820,514 A * | 4/1989 | Cummins | 424/85.4 |
| 2004/0097703 A1 | 5/2004 | Sugiyama | |
| 2004/0247609 A1 | 12/2004 | Sugiyama | |
| 2005/0002951 A1 | 1/2005 | Sugiyama et al. | |
| 2005/0266014 A1 | 12/2005 | Sugiyama et al. | |
| 2008/0070835 A1 | 3/2008 | Sugiyama | |
| 2008/0152631 A1 | 6/2008 | Sugiyama | |
| 2009/0099090 A1 | 4/2009 | Sugiyama et al. | |

FOREIGN PATENT DOCUMENTS

| | | | | |
|---|---|---|---|---|
| EP | 1 004 319 A1 | 5/2000 | | |
| EP | 1 103 564 A1 | 5/2001 | | |
| JP | 61-22018 A | 1/1986 | | |
| JP | 2001-89389 A | 4/2001 | | |
| WO | WO 95/16464 A1 | 6/1995 | | |
| WO | WO 96/02555 A1 | 2/1996 | | |
| WO | WO 99/44634 A1 | 9/1999 | | |
| WO | WO 00/18795 A2 | 4/2000 | | |
| WO | WO 00/26249 A1 | 5/2000 | | |
| WO | WO0026249 | * | 5/2000 | ............ C07K 14/47 |
| WO | WO 00/41463 A2 | 7/2000 | | |
| WO | WO 00/44349 A1 | 9/2000 | | |
| WO | WO 01/49317 A2 | 7/2001 | | |
| WO | WO 01/62920 A2 | 8/2001 | | |
| WO | WO 02/079253 A1 | 10/2002 | | |

OTHER PUBLICATIONS

Takasu (2001, Kurume Med. J. 48(2):171-4).*
Hughes (1998, Veterinary Immunology and Immunopathology 63(1-2):131-138).*
Oka et al, 2000, J Immunol, 164: 1873-1880.*
Ohminami et al, 2000, Blood, 95: 286-293.*
Bergmann et al, 1994 (J Virol, 68(8): 5306-5310).*
Eisenlohr et al, 1992 (J Exp Med, 175: 481-487).*
Shastri et al, 1995 (J Immunol, 155: 4339-4346).*
Guo et al, 1992 (Nature, 360: 364-366).*
Tong et al, 1993, Amer J Med Sci, 306(1): 23-27).*
Gaiger, A et al, 2000 (Blood, 96(4): 1480-1489).*
Lee et al, 1999, J Immunol, 163: 6292-6300.*
Bodey et al, 2000, Anticancer Res, 20: 2665-2676.*
U.S. Appl. No. 11/322,245, filed Jan. 3, 2006, Sugiyama, et al.
U.S. Appl. No. 10/562,486, filed Dec. 27, 2005, Sugiyama.
U.S. Appl. No. 10/527,692, filed Mar. 11, 2005, Sugiyama.
U.S. Appl. No. 10/528,360, filed Mar. 18, 2005, Sugiyama, et al.
U.S. Appl. No. 11/196,452, filed Aug. 4, 2005, Sugiyama, et al.
U.S. Appl. No. 10/541,821, filed Jul. 11, 2005, Sugiyama, et al.
H.-G. Rammensee et al., Immunogenetics, vol. 41, 1995, pp. 178-228.
N. Renkvist et al., Cancer Immunol Immunother, vol. 50, 2001, pp. 3-15.
M. Gessler et al., Nature, vol. 343, Feb. 22, 1990, pp. 774-778.
Y. Oka et al., Immunogenetics, vol. 51, 2000, pp. 99-107.
L. Gao et al., Blood, vol. 95, No. 7, Apr. 1, 2000, pp. 2198-2203.
H. Ohminami et al., Blood, vol. 95, No. 1, Jan. 1, 2000, pp. 286-293.
A. Gaiger et al., Blood, vol. 96, No. 4, Aug. 15, 2000, pp. 1480-1489.
A. Tsuboi et al., Journal of Clinical Immunology, vol. 20, No. 3, 2000, pp. 195-202.
M. Singh et al., Nature Biotechnology, vol. 17, Nov. 1999, pp. 1075-1081.
F.O. Nestle et al., Nature Medicine, vol. 4, No. 3, Mar. 1998, pp. 328-332.
Chem. Abstr., 2002 (Columbus, OH, USA), The abstract No. 2002:880632, Tsuboi, A. et al., "Enhanced Induction of Human WT1-specific cytotoxic T Lympocytes with a 9-mer WT1 peptide modified at HLA-A*2402-binding residues.", Cancer Immunol. Immunother., Dec. 2002, vol. 51, No. 11-12, pp. 614 to 620.
Haruo Sugiyama, "Saibo Shuki to Gan—WT1 Tanpaku o Hyoteki ni shita Gan no Men'eki Ryoho—", Biotherapy, 2000, vol. 14, No. 8, pp. 789 to 795.
Yoshihiro Oka et al., "3. Men'eki Ryoho 2) WT1 o Hyoteki to shita Hakketsubyo ni Taisuru Tokuiteki Men'eki Ryoho", Hematology Frontier, 2000, vol. 10, No. 8, pp. 1017 to 1023.

(Continued)

*Primary Examiner* — Mark Halvorson
(74) *Attorney, Agent, or Firm* — Oblon, Spivak, McClelland, Maier & Neustadt, L.L.P.

(57) ABSTRACT

The present invention provides a method for inducing antigen-specific T cells in a patient comprising administering to said patient in need thereof composition (a) which comprises an antigen protein or an antigen peptide as an active ingredient and composition (b) which comprises a non-specific immunopotentiator as an active ingredient, wherein composition (b) is administered in advance and then composition (a) is administered, as well as related pharmaceutical compositions.

6 Claims, 6 Drawing Sheets

(56) References Cited

OTHER PUBLICATIONS

Oka, Y. et al., "Cancer immunotherapy targeting Wilms' tumor gene WT1 product.", J. Immunol., Feb. 15, 2000, vol. 164. pp. 1873 to 1880.

Sugiyama, H. et al., "Wilms' tumor gene WT1: its oncogenic function and clinical application.", Int. J. Hematol., Feb. 2001, vol. 73, p. 177 to 187.

Lin, R. et al., "Present status of the use of cytokines as adjuvants with vaccines to protect against infectious diseases.", Clin. Infect.Dis., Dec. 1995 vol. 21, No. 6, pp. 1439 to 1449.

Yoshiro Tanio et al., "Men'eki Kyoka Busshitsu", Japanese Journal of Cancer and Chemotherapy, 1980, vol. 7, No. 9, pp. 1710 to 1718.

Ichiro Hagashi, "BRM to shite no Saikin Kintai Seibun", Biomedicine & Therapeutics, 1988, vol. 20, No. 1, pp. 21 to 26.

Mutsuo Hada, et al., "Effect of separate injection of antigen and adjuvant on antibody production", Journal of Radiology and Physical Therapy, vol. 99, XP-001009701, 1975, pp. 97-103 (with English Abstract).

Suzanne L. Elliot, et al., "Peptide based cytotoxic T-cell vaccines; delivery of multiple epitopes, help, memory and problems", Vaccine, vol. 17, XP-002462679, 1999, pp. 2009-2019.

U.S. Appl. No. 12/095,418, filed May 29, 2008, Nishihara, et al.
U.S. Appl. No. 12/181,938, filed Jul. 29, 2008, Sugiyama, et al.
U.S. Appl. No. 11/953,281, filed Dec. 10, 2007, Sugiyama.
U.S. Appl. No. 12/366,200, filed Feb. 5, 2009, Sugiyama, et al.
U.S. Appl. No. 12/552,660, filed Sep. 2, 2009, Sugiyama.
U.S. Appl. No. 12/554,151, filed Sep. 4, 2009, Sugiyama.
U.S. Appl. No. 12/280,268, filed Aug. 21, 2008, Sugiyama.
U.S. Appl. No. 12/521,533, filed Jun. 26, 2009, Sugiyama.
U.S. Appl. No. 12/449,765, filed Aug. 26, 2009, Sugiyama.
U.S. Appl. No. 12/529,701, filed Sep. 2, 2009, Sugiyama.

H. Takasu, "Interferon-α: An Effective Adjuvant for Peptide-Based Cytotoxic T-cell Vaccines", Kurume Medical Journal, vol. 48, 2001, pp. 171-174.

U.S. Appl. No. 09/744,815, filed Jan. 30, 2001, Sugiyama, et al.
U.S. Appl. No. 10/517,600, filed Dec. 13, 2004, Sugiyama, et al.

* cited by examiner

US 8,735,357 B2

METHOD OF INDUCING ANTIGEN-SPECIFIC T CELLS

FIELD OF THE INVENTION

The present invention relates to novel methods of inducing antigen-specific T cells. In particular, the present invention relates to methods of inducing antigen-specific T cells, which administering a composition comprising a non-specific immunopotentiator in advance and then administering a composition comprising an antigen protein or an antigen peptide. In addition, the present invention relates to compositions for treating and/or preventing cancers that are characterized in that they comprise a cancer antigen protein, WT1, or a cancer antigen peptide derived from said WT1 protein in combination with a bacterium-derived component or IFN-α.

BACKGROUND ART

Cellular immunity mediated by, among others, cytotoxic T cells (also sometimes referred to as killer T cells or CTLs) or helper T cells, which are antigen-specific T cells, plays a central role in elimination of cancer cells or virus-infected cells from a living body. An antigen-specific T cell recognizes, using its T cell receptor, a bound complex between an MHC molecule (also referred to as an HLA molecule in case of human) on the cell surface of an antigen-presenting cell such as a dendritic cell or macrophage and an antigen peptide which is a fragment peptide of an antigen protein derived from a cancer or virus, and thereby differentiates and proliferates. Antigen peptides presented on the MHC molecules are known to be usually about 8 to 20 amino acids in length. Antigen-specific T cells that thus have differentiated and proliferated exert their anti-tumor or anti-viral effects by specifically injuring cancerous or virus-infected cells that present the complex bound between the antigen peptide and the MHC molecule, or by producing various cytokines.

So-called vaccine therapies in which an antigen protein or an antigen peptide derived from a cancer or virus is administered to potentiate antigen-specific T cells are believed useful for treatment or prevention of cancers and viral infections. Cancerous or viral antigens recognized by T cells have been screened to date for various cancers and virus infections, and many cancer antigen proteins, virus-derived antigen proteins, and antigen peptides derived therefrom have been already identified (Immunogenetics 1995, 41:178; Cancer Immunol. Immunother. 2001, 50:3). For example, one of those antigens, WT1, was originally identified as a causative gene for a childhood renal tumor, that is, Wilms tumor (Nature 1990, 343:774). In normal tissues, the WT1 gene is weakly expressed only in restricted tissues such as kidney, testis, and ovary, whereas it has been shown to be highly expressed in various cancers such as leukemia as well as lung, breast, ovarian, prostatic, bladder, uterine, cervical, gastric, colon, germ cell, hepatic, and skin cancers (JP Kokai H09-104627, JP Kokai H11-35484). Recently, it has been shown that WT1-specific cytotoxic T cells (CTLs) were induced by in vitro stimulation of peripheral blood mononuclear cells from HLA-A2.1- or HLA-A24.2-positive human donors with a 9-mer WT1 peptide comprising an MHC class I binding motif (Immunogenetics 51:99-107, 2000; Blood 95:2198-203, 2000; Blood 95:286-93, 2000). It has also been shown that WT1-specific CTLs were induced by in vivo immunization of mice with a 9-mer WT1 peptide (J Immunol 164:1873-80, 2000; Blood 96:1480-9, 2000) or WT1 cDNA (J Clin Immunol 20:195-202, 2000), and further that the immunized mice reject transplanted tumor cells highly expressing WT1 (J Immunol 164:1873-80, 2000; J Clin Immunol 20:195-202, 2000). These findings demonstrate that WT1 protein is one of cancer antigen proteins, and may provide a measure for cancer vaccines against fluid or solid cancers.

In order to efficiently induce a specific immunity by vaccination, it is effective to administer an antigen protein or an antigen peptide as a principal agent in combination with a non-specific immunopotentiator. Known non-specific immunopotentiators include bacterium-derived components, cytokines, and plant-derived components. In addition, the dosage form of vaccine is also an important factor for efficient induction of specific immunity. For example, aluminium preparations, lipid particles, emulsion preparations, and microspheres are known as dosage forms of vaccines. These substances and dosage forms that effect the enhancement of vaccine efficacies are collectively called adjuvants (Nature Biotech. 1999, 17:1075). At present, the most widely used adjuvant among those as approved for human use is an aluminium preparation, but its ability to induce antigen-specific T cells is low, and side effects such as IgE production have been pointed out as problems.

In the light of the great ability of dendritic cells as antigen-presenting cells to induce antigen-specific T cells, research on cell vaccines has been also conducted in recent years, in which dendritic cells derived from a patient are pulsed in vitro with an antigen protein or an antigen peptide to cause antigen presentation, and then put back into the patient (Nature Med. 1998, 4:328). However, there are many problems to be solved before the cell vaccine therapy can become widely available; it is technically difficult and costly to obtain a large amount of dendritic cells required for the therapy.

Under such circumstances, there has been a need for developing a novel vaccine that enables simple, convenient, and efficient induction of antigen-specific T cells as well as a method of administering the same.

DISCLOSURE OF THE INVENTION

An object of the present invention is to provide a novel method by which antigen-specific T cells can be efficiently induced. The object is thus to provide a method of inducing antigen-specific T cells which comprises administering a composition comprising a non-specific immunopotentiator in advance and then administering a composition comprising an antigen protein or an antigen peptide. A further object of the present invention is to provide a composition for treating and/or preventing cancers that is characterized in that it comprises a cancer antigen protein, WT1, or a cancer antigen peptide derived from said WT1 protein in combination with a bacterium-derived component or IFN-α.

In order to elicit immune responses to a vaccine, it is important to timely administer an antigen in an appropriate form. As described above, however, there has not been known any method of administering a vaccine that efficiently induces antigen-specific T cells and thereby produces anti-tumor or anti-viral effects.

The present inventors therefore concentrated their efforts on examining therapeutic effects on an in vivo cancer model, of cancer antigen peptides derived from the cancer antigen protein WT1, as used as an example. As a result, it was found for the first time that antigen-specific T cells can be efficiently induced in vivo, leading for example to anti-tumor effects, by administering an immunopotentiator in advance and, after a certain period, administering an antigen peptide. It was also found that all of five different components distinct in origin and properties used as the immunopotentiator could consistently exhibit remarkable anti-tumor effects, when administered in advance of the antigen administration.

Furthermore, in the present invention, the cancer antigen protein WT1 was, for the first time, examined for its effects in a cancer model that reflects, so to speak, "a therapeutic system" in which a cancer antigen peptide derived from WT1 is administered after transplantation of tumor cells into an animal. As a result, it was demonstrated for the first time that WT1 is therapeutically effective. In addition, the cancer antigen peptides derived from said WT1 protein were also found to produce remarkable anti-tumor effects when administered in combination with a bacterium-derived component or IFN-α used as an adjuvant.

The present invention is based on such findings as described above.

Thus, the present invention relates to:

(1-1) a method for inducing antigen-specific T cells in a patient comprising administering to said patient in need thereof:
composition (a) which comprises an antigen protein or an antigen peptide as an active ingredient and
composition (b) which comprises a non-specific immunopotentiator as an active ingredient, wherein said composition (b) is administered in advance and then, for example, about 24 hours after the administration, said composition (a) is administered; for example, the method wherein compositions (a) and (b) are both administered at the same subcutaneous site (the administration cycle involving compositions (a) and (b) may be repeated two or more times); preferably, the method wherein composition (a) comprises a cancer antigen protein or a cancer antigen peptide as an active ingredient; more preferably, the method wherein the cancer antigen protein or the cancer antigen peptide is WT1 protein set forth in SEQ ID NO: 1 or a cancer antigen peptide derived from said WT1 protein; and still more preferably, the method wherein the cancer antigen peptide derived from WT1 is selected from a group consisting of Arg Met Phe Pro Asn Ala Pro Tyr Leu (SEQ ID NO: 2), Cys Met Thr Trp Asn Gln Met Asn Leu (SEQ ID NO: 3), and Cys Tyr Thr Trp Asn Gln Met Asn Leu (SEQ ID NO: 4);

the method wherein the non-specific immunopotentiator which is the active ingredient of composition (b) is selected from a group consisting of (i) a bacterium-derived component or a derivative thereof, (ii) a cytokine, (iii) a plant-derived component or a derivative thereof, and (iv) a marine organism-derived component or a derivative thereof; preferably, the method wherein the bacterium-derived component is selected from a group consisting of human tubercle *bacillus*-derived polysaccharide materials (e.g. Ancer), hemolytic *streptococcus* powders (e.g. Picibanil), basidiomycete-derived polysaccharides (e.g. lentinan, Krestin), dead microbial suspension cocktails (e.g. Broncasma Berna), muramyl-dipeptide (MDP)-related compounds, lipopolysaccharides (LPS), lipid A-related compounds (e.g. MPL), a glycolipid trehalose dimycolate (TDM), and DNAs derived from the above-mentioned bacteria (e.g. CpG oligonucleotide); preferably, the method wherein the cytokine is selected from a group consisting of IFN-α, IL-12, GM-CSF, IL-2, IFN-γ, IL-18, and IL-15; preferably, the method wherein the marine organism-derived component is α-galactosylceramide;

In particular, a method of treatment and/or prevention of a cancer in a patient which comprises any one of the induction methods as described above;

in another embodiment, (1-2) a pharmaceutical composition for enhancing an activity of an antigen protein or an antigen peptide to induce antigen-specific T cells, which comprises a non-specific immunopotentiator as an active ingredient and is administered before the administration of the antigen protein or the antigen peptide; or a pharmaceutical composition for enhancing an anticancer activity based on the immunopotentiating action of a non-specific immunopotentiator, which comprises an antigen protein or an antigen peptide as an active ingredient, of which the activity to induce antigen-specific T cells facilitates the enhancement of the anticancer activity, said composition being administered after the administration of said non-specific immunopotentiator;

preferably, the pharmaceutical composition wherein the antigen protein or the antigen peptide is a cancer antigen protein or a cancer antigen peptide; more preferably, the pharmaceutical composition wherein the cancer antigen protein or the cancer antigen peptide is WT1 protein set forth in SEQ ID NO: 1 or a cancer antigen peptide derived from said WT1 protein; and still more preferably, the pharmaceutical composition wherein the cancer antigen peptide derived from WT1 is selected from a group consisting of Arg Met Phe Pro Asn Ala Pro Tyr Leu (SEQ ID NO: 2), Cys Met Thr Trp Asn Gln Met Asn Leu (SEQ ID NO: 3), and Cys Tyr Thr Trp Asn Gln Met Asn Leu (SEQ ID NO: 4);

preferably, the pharmaceutical composition wherein the non-specific immunopotentiator is selected from a group consisting of (i) a bacterium-derived component or a derivative thereof, (ii) a cytokine, (iii) a plant-derived component or a derivative thereof, and (iv) a marine organism-derived component or a derivative thereof; specifically, the pharmaceutical composition wherein the bacterium-derived component is selected from a group consisting of human tubercle *bacillus*-derived polysaccharide materials (e.g. Ancer), hemolytic *streptococcus* powders (e.g. Picibanil), basidiomycete-derived polysaccharides (e.g. lentinan, Krestin), dead microbial suspension cocktails (e.g. Broncasma Berna), muramyl-dipeptide (MDP)-related compounds, lipopolysaccharides (LPS), lipid A-related compounds (e.g. MPL), a glycolipid trehalose dimycolate (TDM), and DNAs derived from the above-mentioned bacteria (e.g. CpG oligonucleotide); specifically, the pharmaceutical composition wherein the cytokine is selected from a group consisting of IFN-α, IL-12, GM-CSF, IL-2, IFN-γ, IL-18, and IL-15; specifically, the pharmaceutical composition wherein the marine organism-derived component is α-galactosylceramide;

specifically, the pharmaceutical composition as described above for treatment and/or prevention of a cancer; and in another embodiment, (1-3) a use of a non-specific immunopotentiator for preparing a medicament which is administered before the administration of an antigen protein or an antigen peptide and which enhances an activity of the antigen protein or the antigen peptide to induce antigen-specific T cells; or a use of an antigen protein or an antigen peptide for preparing a medicament which is administered after the administration of a non-specific immunopotentiator and which enhances an anticancer activity based on the immunopotentiating action of said non-specific immunopotentiator by means of the activity of the protein or the peptide to induce antigen-specific T cells; and embodiments corresponding to the embodiments as preferably or specifically described in (1-2); and in a still further embodiment, (2-1) a pharmaceutical composition for enhancing an activity of WT1 protein set forth in SEQ ID NO: 1 or a cancer antigen peptide derived from said WT1 protein to induce antigen-specific T cells, which comprises a bacterium-derived component or a derivative thereof as an active ingredient; or a pharmaceutical composition for enhancing an anticancer activity based on the immunopotentiating action of a bacterium-derived component or a derivative thereof, which comprises as an active ingredient WT1 protein set forth in SEQ ID NO: 1 or a cancer antigen peptide derived from said WT1 protein, of which the activity to induce antigen-specific T cells facilitates the enhancement of the anticancer activity; preferably, the pharmaceutical composition wherein the bacterium-derived component is a human tubercle *bacillus*-derived polysaccharide material (e.g. Ancer), a hemolytic *streptococcus* powder (e.g. Picibanil), a basidiomycete-derived polysaccharide (e.g. lentinan, Krestin), or a dead microbial suspension cocktail (e.g. Broncasma Berna); and a pharmaceutical composition for enhancing an activity of WT1 protein set forth in SEQ ID NO: 1 or a cancer antigen peptide derived from said WT1 protein to induce antigen-specific T cells, which comprises IFN-α as an active ingredient; or a pharmaceutical composition for enhancing an anticancer activity based on the immunopotentiating action of IFN-α, which comprises as an active ingredient WT1 protein set forth in SEQ ID NO: 1 or a cancer antigen peptide derived from said WT1 protein, of which the activity to induce antigen-specific T cells facilitates the enhancement of the anticancer activity;

preferably, the pharmaceutical composition wherein the cancer antigen peptide derived from WT1 is selected from a group consisting of Arg Met Phe Pro Asn Ala Pro Tyr Leu (SEQ ID NO: 2), Cys Met Thr Trp Asn Gln Met Asn Leu (SEQ ID NO: 3), and Cys Tyr Thr Trp Asn Gln Met Asn Leu (SEQ ID NO: 4); specifically, the pharmaceutical composition for treatment and/or prevention of a cancer as described above;

in another embodiment, (2-2) a method for enhancing, in a patient, an activity of WT1 protein set forth in SEQ ID NO: 1 or a cancer antigen peptide derived from said WT1 protein to induce antigen-specific T cells, which comprising administering to said patient a bacterium-derived component or a derivative thereof in an amount effective to enhance the activity to induce antigen-specific T cells;

a method for enhancing, in a patient, an anticancer activity based on the immunopotentiating action of a bacterium-derived component or a derivative thereof, which comprises administering to said patient WT1 protein set forth in SEQ ID NO: 1 or a cancer antigen peptide derived from said WT1 protein in an amount effective to enhance the anticancer activity based on the immunopotentiating action wherein the enhancement of the anticancer activity is facilitated by the activity to induce antigen-specific T cells;

a method for enhancing, in a patient, an activity of WT1 protein set forth in SEQ ID NO: 1 or a cancer antigen peptide derived from said WT1 protein to induce antigen-specific T cells, which comprises administering to said patient IFN-α in an amount effective to enhance the activity to induce antigen-specific T cells;

a method for enhancing, in a patient, an anticancer activity based on the immunopotentiating action of IFN-α, which comprises administering to said patient WT1 protein set forth in SEQ ID NO: 1 or a cancer antigen peptide derived from said WT1 protein in an amount effective to enhance the anticancer activity based on the immunopotentiating action, wherein the enhancement of the anticancer activity is facilitated by the activity to induce antigen-specific T cells;

the method as described above wherein the agents are administered to a cancer patient for treatment and/or prevention of a cancer; and embodiments corresponding to the embodiments preferably and specifically described above in (2-1); and in another embodiment, (2-3) a use of a bacterium-derived component or a derivative thereof for preparing a medicament which enhances an activity of WT1 protein set forth in SEQ ID NO: 1 or a cancer antigen peptide derived from said WT1 protein to induce antigen-specific T cells;

a use of WT1 protein set forth in SEQ ID NO: 1 or a cancer antigen peptide derived from said WT1 protein for preparing a medicament which enhances an anticancer activity based on the immunopotentiating action of a bacterium-derived component or a derivative thereof by means of the activity of the protein or the peptide to induce antigen-specific T cells;

a use of IFN-α for preparing a medicament which enhances an activity of WT1 protein set forth in SEQ ID NO: 1 or a cancer antigen peptide derived from said WT1 protein to induce antigen-specific T cells; and a use of WT1 protein set forth in SEQ ID NO: 1 or a cancer antigen peptide derived from said WT1 protein for preparing a medicament which enhances an anticancer activity based on the immunopotentiating action of IFN-α by means of the activity of the protein or the peptide to induce antigen-specific T cells; and embodiments corresponding to the preferred and the specific embodiments described above in (2-1).

BEST MODE FOR CARRYING OUT THE INVENTION

Figure 1:
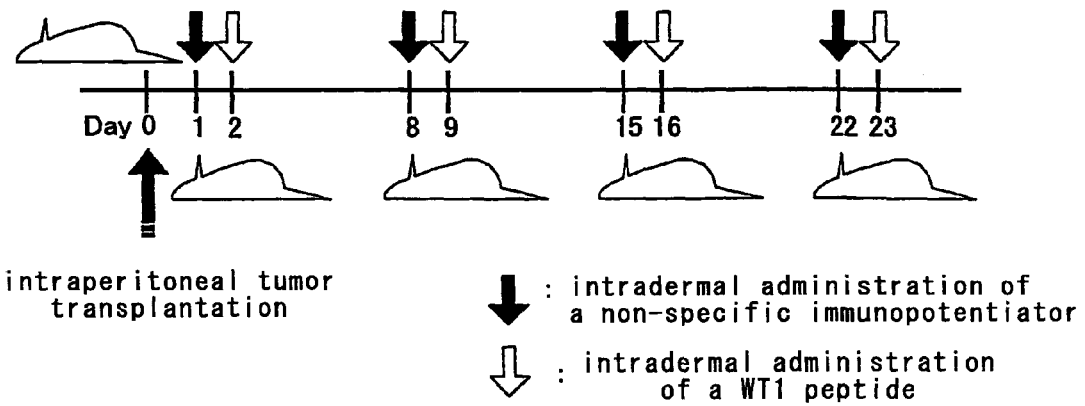
FIG. 1 shows a schedule for transplantation of tumor cells and vaccination with a WT1 peptide and one of immunopotentiators.

As described above, according to a first aspect, the present invention provides a method for inducing antigen-specific T cells in a patient comprising administering to said patient in need thereof composition (a) which comprises a therapeutically effective amount of an antigen protein or an antigen peptide as an active ingredient and composition (b) which comprises a therapeutically effective amount of a non-specific immunopotentiator as an active ingredient, wherein said composition (b) is administered in advance and then said composition (a) is administered. This method is characterized in that it comprises an administration procedure in which the non-specific immunopotentiator as an adjuvant is administered in advance, and then, after a certain period, an antigen (an antigen protein or antigen peptide derived from said antigen protein) is administered. The administration procedure of the present invention can produce an antigen-specific T cell-inducing effect and thus an anti-tumor or antiviral effect better than those obtained with the antigen alone or the non-specific immunopotentiator alone.

The term "antigen protein or peptide" comprised as an active ingredient in composition (a) refers to an antigen protein and an antigen peptide derived from said antigen protein, and is not specifically limited so long as it is capable of inducing T cells specific for an antigen peptide. In addition, the term "antigen protein or antigen peptide" also includes within its scope those capable of inducing antigen-specific T cells directly by forming a complex with an MHC molecule (HLA molecule) on the cell surface of an antigen-presenting cell as well as those capable of inducing antigen-specific T cells indirectly, that is, by being incorporated into the cell and intracellularly degraded to a peptide fragment which binds an MHC molecule to form a complex presented on the cell surface.

Antigen proteins include, for example, antigen proteins derived from viruses, antigen protein derived from bacteria, or cancer antigen proteins (also known as tumor antigen proteins). Several proteins already known as antigen proteins are listed below. Examples of antigen proteins derived from viruses are those derived from HIV, hepatitis C virus, hepatitis B virus, influenza virus, HPV, HTLV, and EBV. Examples of antigen proteins derived from bacteria are those derived from tubercle bacilli. Representative examples of cancer antigen proteins are those listed in Table 1 of Immunity, vol. 10: 281, 1999, or those listed in Tables 1 to 6 of Cancer Immunol. Immunother., vol. 50, 3-15, 2001. More specifically, melanoma antigen proteins include MAGE (Science, 254:1643, 1991), gp100 (J. Exp. Med., 179:1005, 1994), MART-1 (Proc. Natl. Acad. Sci. USA, 91:3515, 1994), and tyrosinase (J. Exp. Med., 178:489, 1993); and cancer antigen proteins other than those derived from melanoma includes tumor makers such as HER2/neu (J. Exp. Med., 181:2109, 1995), CEA (J. Natl. Cancer. Inst., 87:982, 1995), and PSA (J. Natl. Cancer. Inst., 89:293, 1997), as well as SART-1 derived from squamous cell carcinoma (J. Exp. Med., vol. 187, p. 277-288, 1998; WO 97/46676), cyclophilin B (Proc. Natl. Acad. Sci., U.S.A. 88:1903, 1991), SART-3 (Cancer Res., vol. 59, 4056 (1999)), and WT1 (Immunogenetics, vol. 51, 99, 2000; Blood 95:2198-203, 2000; Blood 95: 286-93, 2000, or human WT1 set forth in the Sequence Listing of the present application as SEQ ID NO: 1). In addition to the above antigen proteins in their full-length forms, partial polypeptides or alterations thereof are also included so long as they are capable of inducing T cells specific for an antigen peptide.

Such antigen proteins may be obtained, according to the references cited above or to standard texts such as Molecular Cloning 2nd Ed., Cold Spring Harbor Laboratory Press (1989), through the following steps: cloning a cDNA encoding a desired antigen protein, ligating the cDNA into an expression vector, introducing the resulting recombinant expression vector into a host cell, and expressing the antigen protein. More specifically, for example, a cDNA encoding a desired antigen protein is cloned by hybridization or a PCR method. The cloned cDNA is then incorporated into an appropriate expression vector (e.g. pSV-SPORT1). The resulting recombinant expression vector is introduced into a host cell, and the transformants thus obtained may be cultured in an appropriate medium to express and produce the desired antigen protein. In this context, host cells include, for example, prokaryotes such as E. coli, unicellular eukaryotes such as yeasts, and multicellular eukaryotic cells such as those of insects or animals. Methods of gene transfer into host cells include, for example, the calcium phosphate, DEAE-dextran, and electric pulse methods. Polypeptides thus obtained can be isolated and purified using standard biochemical techniques.

The in vitro ability of such antigen proteins to induce antigen-specific T cells can be examined, for example, in the case of cancer antigen proteins, by a test as described below. Thus, first, certain cells which express no cancer antigen protein such as COS-7 derived from African green monkey kidney (ATCC CRL1651) or fibroblast VA-13 (RIKEN Cell Bank, The Institute of Physical and Chemical Research) are double transfected with a recombinant expression vector which comprises cDNA encoding a desired cancer antigen protein and a recombinant expression vector which comprises DNA encoding an HLA antigen. Such transfection may be achieved by the Lipofectin method using Lipofectamine reagent (GIBCO BRL). Subsequently, tumor-reactive CTLs restricted by the HLA molecule used are added and allowed to act. The amounts of various cytokines (e.g. IFN-γ) produced by said CTLs in response may be then measured, for example, by an ELISA method, in order to evaluate an activity of the desired cancer antigen protein to induce antigen-specific T cells.

Antigen peptides derived from antigen proteins (hereinafter simply referred to as antigen peptides) include, for example, peptides of about 8 to 20 amino acid residues which are part of said antigen proteins, or altered peptides thereof having functionally equivalent properties, or polytopes in which two or more of said peptides or altered peptide thereof are linked together. In this definition, the range "8 to 20" is based on the common knowledge among those skilled in the art that antigen peptides presented by MHC molecules are usually about 8 to 20 amino acids in length. The term "altered peptide having functionally equivalent properties" means an altered peptide in which one to several amino acid residues in the amino acid sequence of an antigen peptide have been substituted, deleted, and/or added (including addition to the amino acid at the N- or C-terminal end of the peptide) and which is capable of inducing T cells specific for an antigen peptide.

In cancer antigen peptides and virus-derived antigen peptides, certain rules (motifs) in the sequences of antigen peptides bound and presented by an HLA molecule are known for certain HLA types such as HLA-A1, -A0201, -A0204, -A0205, -A0206, -A0207, -A11, -A24, -A31, -A6801, -B7, -B8, -B2705, -B37, -Cw0401, and -Cw0602 (see, e.g., Immunogenetics, 41:178, 1995). For example, regarding a motif for HLA-A24, it is known that the amino acid at position 2 in a peptide consisting of 8 to 11 amino acids is tyrosine, phenylalanine, methionine, or tryptophan, and the amino acid at the C-terminal end is phenylalanine, leucine, isoleucine, tryptophan, or methionine (J. Immunol., 152, p. 3913, 1994; Immunogenetics, 41, p. 178, 1995; J. Immunol., 155, p. 4307, 1994). Likewise, regarding HLA-A2, motifs listed below in Table 1 are known (Immunogenetics, 41, p. 178, 1995; J. Immunol., 155, p. 4749, 1995).

TABLE 1

| Type of HLA-A2 | Amino acid at position 2 from the N-terminal end | Amino acid at the C-terminal end |
|---|---|---|
| HLA-A0201 | L, M | V, L |
| HLA-A0204 | L | L |
| HLA-A0205 | V, L, I, M | L |
| HLA-A0206 | V, Q | V, L |
| HLA-A0207 | L | L | the peptides are 8 to 11 amino acids in length

Furthermore, in recent years, peptide sequences expected to be able to bind HLA antigens can be searched on the internet by using a software of BIMAS at NIH. It is also possible to conduct a search by using BIMAS HLA peptide binding prediction analysis (J. Immunol., 152, 163, 1994).

It is therefore easy to select antigen peptide portions involved in these motifs from the amino acid sequences of the cancer antigen proteins or virus-derived antigen proteins as described above. Specific examples of antigen peptides thus selected, in particular, for example, of cancer antigen peptides, are as follows. Examples of cancer antigen peptides derived from WT1 are peptides listed in Table II to Table XLVI of WO 2000/18795, and in particular, peptides having the HLA-A24 and HLA-A2 binding motifs set forth in the Sequence Listing of the present application as SEQ ID NOs: 2 and 3. Examples of cancer antigen peptides derived from SART-1 are peptides listed in the Sequence Listings of WO 97/46676, WO 2000/02907, and WO 2000/06595. Examples of cancer antigen peptides derived from cyclophilin B are peptides listed in the Sequence Listing of WO 99/67288. Examples of cancer antigen peptides derived from SART-3 are peptides listed in the Sequence Listing of WO 2000/12701. By subjecting the above peptides to an activity measurement described below, one can select antigen peptides having an activity to induce antigen-specific T cells.

In addition, where certain rules (motifs) in the antigen peptide sequences that are bound and presented by an HLA molecule are known as described above, altered peptides having properties functionally equivalent to those of the above antigen peptides may be exemplified by altered peptides in which one or more of amino acids have been substituted on the basis of said motifs. Thus, in the case of a binding motif for HLA-A24, for example, it is known as described above that the amino acid at position 2 in a peptide consisting of 8 to 11 amino acids is tyrosine, phenylalanine, methionine, or tryptophan, and the amino acid at the C-terminal end is phenylalanine, leucine, isoleucine, tryptophan, or methionine (J. Immunol., 152, p. 3913, 1994; Immunogenetics, 41, p. 178, 1995; J. Immunol., 155, p. 4307, 1994). Therefore, altered peptides bound and presented by the HLA-A24 antigen may be exemplified by those in which one or more amino acids at position 2 and at the C-terminal end of an HLA-A24-restricted wild-type peptide have been substituted within the amino acids listed above. Specific examples of such altered peptides, for example, in connection with cancer antigens, are as follows. Examples of altered peptides derived from WT1 are those obtained by modifying the peptides listed in Table II to Table XLVI of WO2000/18795 on the basis of the above motif, and in particular, a peptide having the amino acid sequence set forth in the Sequence Listing of the present application as SEQ ID NO: 4. Likewise, examples of altered peptides derived from, for example, SART-1, cyclophilin B, or SART-3 are those obtained by modifying respective antigen peptides disclosed in the above references on the basis of the motif. Such altered peptides are also included within the scope of antigen peptides of the present invention.

Antigen peptides (including altered peptides) as described above may be prepared according to the methods usually used in peptide chemistry. Examples of such methods are those described in references, for example, "Peptide Synthesis", Interscience, New York, 1966; "The Proteins", Vol. 2, Academic Press Inc., New York, 1976; "Peputido-Gosei", Maruzen, 1975; "Pepuchido-Gosei-no-Kiso-to-Jikken", Maruzen, 1985; and "Iyakuhin-no-Kaihatu, Zoku, Vol. 14, Peputido-Gosei", Hirokawa Shoten, 1991. Alternatively, such peptides may also be prepared according to "Molecular Cloning" cited above by expressing a recombinant peptide from a DNA encoding the antigen peptide and purifying it using routine procedures.

The in vitro ability of such antigen peptides to induce antigen-specific T cells can be examined, for example, in the case of cancer antigen peptides, by an assay described, for example, in J. Immunol., 154, p. 2257, 1995. In particular, peripheral blood lymphocytes may be isolated from an HLA antigen-positive human, and stimulated in vitro by adding a peptide of interest. If CTLs that specifically recognize the HLA-positive cells pulsed with the peptide are induced, the peptide can be thereby confirmed to have an activity to induce antigen-specific T cells. The presence or absence of CTL induction may be determined, for example, by measuring the amount of IFN-γ produced by CTLs in response to the antigen peptide-presenting cells using an enzyme-linked immunosorbent assay (ELISA). Alternatively, the amount of TNF-α produced by CTLs in response to the antigen peptide-presenting cells may be determined by measuring the survival rate of a TNF-α sensitive cell line (e.g. WEHI164S cells; ATCC Cat. No. CRL-1751).

Determination may also be achieved by a method in which the cytotoxicity of CTLs against antigen peptide-presenting cells labeled with $^{51}$Cr is measured ($^{51}$Cr release assay; Int. J. Cancer, 58:317, 1994). Alternatively, for example, COS-7 (ATCC No. CRL1651) or VA-13 (RIKEN Cell Bank, The Institute of Physical and Chemical Research) cells into which an expression plasmid expressing cDNA for HLA has been introduced are pulsed with a peptide of interest. Then, for example, the CTLs prepared as described above may be reacted with the pulsed cells, and the amounts of various cytokines (e.g. IFN-γ or TNF-α) produced by said CTLs may be measured.

The term "polytope" means a recombinant peptide in which two or more antigen peptides have been linked together (see, e.g., Journal of Immunology, 160, p. 1717, 1998), and particularly in the present invention refers to a polypeptide which appropriately combines one, two or more kinds of the above antigen peptides. A polytope is obtained by a procedure in which a recombinant DNA prepared by linking together one, two or more kinds of DNAs encoding the above antigen peptides is inserted into an appropriate expression vector, and the recombinant vector obtained is then expressed in a host cell. Activity of the polytope to induce antigen-specific T cells may be confirmed by subjecting it to the assay for antigen protein as described above. These polytopes may also be used as antigen peptides in the present invention.

At least one kind of antigen protein or peptide as described above is selected and used as an active ingredient in the above composition (a). Depending on the purpose, two or more kinds of antigen proteins or peptides may be present. Although a therapeutically effective amount of such antigen proteins or peptides is not specifically limited so long as it is capable of inducing in vivo antigen-specific T cells, it is preferably usually 0.0001 mg to 1000 mg, more preferably 0.001 mg to 100 mg, still more preferably 0.01 mg to 10 mg.

The above composition (a) is preferably formulated into a dosage form that achieves desired pharmacological effects. Dosage forms suitable for this purpose include, for example, formulations such as water-in-oil (w/o) emulsions, oil-in-water (o/w) emulsions, and water-in-oil-in-water (w/o/w) emulsions, as well as liposome formulations, microsphere formulations, microcapsule formulations, solid injections and liquid formulations.

Water-in-oil (w/o) emulsion formulations take the form in which an active ingredient is dispersed in an aqueous dispersed phase. Oil-in-water (o/w) emulsion formulations take the form in which an active ingredient is dispersed in an aqueous dispersion medium. Likewise, water-in-oil-in-water (w/o/w) emulsion formulations take the form in which an active ingredient is dispersed in the inner-most aqueous dispersed phase. Preparation of such formulations may be achieved by referring to, for example, JP Kokai H08-985, JP Kokai H09-122476, etc.

Liposome formulations are microparticles in the form in which an active ingredient is incorporated in an aqueous phase or within membranes by means of liposomes having a lipid bilayer structure. Examples of principal lipids for preparing liposomes are phosphatidylcholine and sphingomyelin, to which, for example, dicetyl phosphate, phosphatidic acid, or phosphatidylserine is added to provide liposomes with electric charges for stabilization. Exemplary methods for preparing liposomes are ultrasonication, ethanol injection, ether injection, reverse-phase evaporation, and French press extraction methods.

Microsphere formulations are microparticles made of a homogeneous polymer matrix in which an active ingredient is dispersed. Examples of components for the matrix are biodegradable polymers such as albumin, gelatin, chitin, chitosan, starch, polylactic acid, and polyalkyl cyanoacrylate. Preparation of microsphere formulations may be carried out according to known methods (Eur. J. Pharm. Biopharm. 50:129-146, 2000; Dev. Biol. Stand. 92:63-78, 1998; Pharm. Biotechnol. 10:1-43, 1997) and is not specifically limited.

Microcapsule formulations are microparticles in the form in which an active ingredient as a core substance is covered with an encapsulating substance. Examples of a coating material used as an encapsulating substance are membrane-forming polymers such as carboxymethylcellulose, cellulose acetate phthalate, ethylcellulose, gelatin, gelatin-acacia, nitrocellulose, polyvinyl alcohol, and hydroxypropylcellulose. Microcapsule formulations may be prepared according to, for example, the coacervation or interfacial polymerization method.

Solid injections are dosage forms in which an active ingredient is included in a base material such as collagen or silicone to solidify the forms. Solid injections may be prepared according to, for example, a method described in a reference (Pharm. Tech. Japan, 7 (1991), p. 402-409).

Liquid formulations are dosage forms in which an active ingredient is mixed with a pharmaceutically acceptable solvent, carrier, or the like. Examples of a pharmaceutically acceptable solvent include water, a glucose solution, and physiological saline. In addition, liquid formulations may comprise a pharmaceutically acceptable auxiliary agent such as a pH regulating agent or buffer, a tonicity adjusting agent, or a swelling agent.

Furthermore, composition (a) may also take the form of a lyophilized formulation corresponding to the above dosage forms. Other agents such as a stabilizing agent (e.g. polysaccharides, amino acids, proteins, urea, or sodium chloride), an excipient (e.g. sugars, amino acids, urea, or sodium chloride), an antioxidant, an antiseptic, an isotonizing agent, or an buffer may also be added according to the necessity.

Such composition (a) as described above may be used as a pre-formulated product or may be prepared before use for administration to a patient. Thus, the antigen protein or the antigen peptide as an active ingredient of composition (a) as well as an emulsion or other preparation as the dosage form may be used as a pre-formed product in which the constituents have already been mixed together, or may be prepared before use for administration to a patient.

Now, composition (b), that is, a composition comprising as an active ingredient a non-specific immunopotentiator is described below.

The "non-specific immunopotentiator" comprised as an active ingredient in composition (b) is not specifically limited so long as it is a substance having an enhancing effect on an activity of an antigen protein or an antigen peptide to induce antigen-specific T cells. In particular, examples include (i) a bacterium-derived component or a derivative thereof, (ii) a cytokine, (iii) a plant-derived component or a derivative thereof, or (iv) a marine organism-derived component or a derivative thereof.

"Bacterium-derived components or a derivative thereof" having an enhancing effect on an activity to induce antigen-specific T cells may be categorized, for example, into (1) dead bodies of bacteria, (2) cell wall skeleton (abbreviated as CWS) derived from bacteria, (3) particular components derived from microbial bodies, or derivatives thereof.

In this connection, examples of (1) dead bodies of bacteria include hemolytic *streptococcus* powders (e.g. Picibanil; Chugai Pharmaceuticals Co.), dead microbial suspension cocktails (e.g. Broncasma Berna; Sanwa Kagaku Kenkyusho Co.), or dead bodies of human tubercle bacilli.

Examples of (2) CWS derived from bacteria include CWS derived from the genus *Mycobacterium* (e.g. CWS of the BCG strain of *Mycobacterium bovis*), CWS derived from the genus *Nocardia* (e.g. CWS of *Nocardia rubra*), or CWS derived from the genus *Corynebacterium*.

Examples of (3) particular components derived from microbial bodies or derivatives thereof include microbial-derived polysaccharides such as a human tubercle *bacillus*-derived polysaccharide material (e.g. Ancer; Zeria Pharmaceutical Co.) and basidiomycete-derived polysaccharides (e.g. lentinan; Ajinomoto, Krestin; Sankyo Co., *Coriolus versicolor*), or muramyldipeptide (MDP)-related compounds, lipopolysaccharides (LPS), lipid A-related compounds (MPL), a glycolipid trehalose dimycolate (TDM), and DNAs derived from bacteria (e.g. CpG oligonucleotides), or derivatives thereof.

These bacterium-derived components and their derivatives may be obtained as commercially available products, if possible, or may be isolated or prepared according to, for example, known references (e.g. Cancer Res., 33, 2187-2195 (1973); J. Natl. Cancer Inst., 48, 831-835 (1972); J. Bacteriol., 94, 1736-1745 (1967); Gann, 69, 619-626 (1978); J. Bacteriol., 92, 869-879 (1966); J. Natl. Cancer Inst., 52, 95-101 (1974)).

Examples of "cytokines" having an enhancing effect on an activity to induce antigen-specific T cells are IFN-α, IL-12, GM-CSF, IL-2, IFN-γ, IL-18, and IL-15. These cytokines may have natural origin or may be recombinant products. These cytokines may be obtained and used as commercially available products, if possible. In the case of recombinant products, based on respective base sequences deposited in databases such as GenBank, EMBL, or DDBJ, a desired gene may be cloned by a routine method, and ligated into an appropriate expression vector. The resulting recombinant expression vector may be then used to transform a host cell such that the desired product is expressed and produced.

Examples of "a plant-derived component or a derivative thereof" having an enhancing effect on an activity to induce antigen-specific T cells are saponin-derived components such as Quil A (Accurate Chemical 86 Scientific Corp.), QS-21 (Aquila Biopharmaceuticals Inc.), and glycyrrhizin (Sigma-Aldrich).

Examples of "a marine organism-derived component or a derivative thereof" having an enhancing effect on an activity to induce antigen-specific T cells are glycolipids derived from sponges, and specifically, α-galactosylceramide (J. Med. Chem., 1995 Jun. 9, 38(12) p. 2176-2787).

At least one kind non-specific immunopotentiator as described above is selected and used as an active ingredient in the above composition (b). Depending on the purpose, two or more kinds of non-specific immunopotentiators may be present. Although a therapeutically effective amount of such non-specific immunopotentiators is not specifically limited so long as it has in vivo enhancing activity on induction of antigen-specific T cells, it is preferably usually 0.0001 mg to 1000 mg, more preferably 0.001 mg to 100 mg, still more preferably 0.01 mg to 10 mg. Likewise, in the case of the above cytokines, an exemplary potency may be about 10 U to $1 \times 10^8$ Upper dose.

The above composition (b) is preferably formulated into a dosage form that achieves desired pharmacological effects. Dosage forms suitable for this purpose include, for example, formulations such as water-in-oil (w/o) emulsions, oil-in-water (o/w) emulsions, and water-in-oil-in-water (w/o/w) emulsions, as well as liposome formulations, microsphere formulations, microcapsule formulations, solid injections and liquid formulations.

Water-in-oil (w/o) emulsion formulations take the form in which an active ingredient is dispersed in an aqueous dispersed phase. Oil-in-water (o/w) emulsion formulations take the form in which an active ingredient is dispersed in an aqueous dispersion medium. Likewise, water-in-oil-in-water (w/o/w) emulsion formulations take the form in which an active ingredient is dispersed in the inner-most aqueous dispersed phase. Preparation of such formulations may be achieved by referring to, for example, JP Kokai H08-985, JP Kokai H09-122476, etc.

Liposome formulations are microparticles in the form in which an active ingredient is incorporated in an aqueous phase or within membranes by means of liposomes having a lipid bilayer structure. Examples of principal lipids for preparing liposomes are phosphatidylcholine and sphingomyelin, to which, for example, dicetyl phosphate, phosphatidic acid, or phosphatidylserine is added to provide liposomes with electric charges for stabilization. Exemplary methods for preparing liposomes are ultrasonication, ethanol injection, ether injection, reverse-phase evaporation, and French press extraction methods.

Microsphere formulations are microparticles made of a homogeneous polymer matrix in which an active ingredient is dispersed. Examples of materials for the matrix are biodegradable polymers such as albumin, gelatin, chitin, chitosan, starch, polylactic acid, and polyalkyl cyanoacrylate. Preparation of microsphere formulations may be carried out according to known methods (Eur. J. Pharm. Biopharm. 50:129-146, 2000; Dev. Biol. Stand. 92:63-78, 1998; Pharm. Biotechnol. 10:1-43, 1997) and is not specifically limited.

Microcapsule formulations are microparticles in the form in which an active ingredient as a core substance is covered with an encapsulating substance. Examples of a coating material used as an encapsulating substance are membrane-forming polymers such as carboxymethylcellulose, cellulose acetate phthalate, ethylcellulose, gelatin, gelatin-acacia, nitrocellulose, polyvinyl alcohol, and hydroxypropylcellulose. Microcapsule formulations may be prepared according to, for example, the coacervation or interfacial polymerization method.

Solid injections are dosage forms in which an active ingredient is included in a base material such as collagen or silicone to solidify the forms. Solid injections may be prepared according to, for example, a method described in a reference (Pharm. Tech. Japan, 7 (1991), p. 402-409).

Liquid formulations are dosage forms in which an active ingredient is mixed with a pharmaceutically acceptable solvent, carrier, or the like. Examples of a pharmaceutically acceptable solvent include water, a glucose solution, and physiological saline. In addition, liquid formulations may comprise a pharmaceutically acceptable auxiliary agent such as a pH regulating agent or buffer, a tonicity adjusting agent, or a swelling agent.

Among these dosage forms, preferred are water-in-oil (w/o) emulsion formulations, oil-in-water (o/w) emulsion formulations, water-in-oil-in-water (w/o/w) emulsion formulations, or microsphere formulations. Such dosage forms are particularly preferred if the non-specific immunopotentiator is a bacterium-derived component, a plant-derived component, or a derivative thereof.

Furthermore, composition (b) may also take the form of a lyophilized formulation corresponding to the above dosage forms. Other agents such as a stabilizing agent (e.g. polysaccharides, amino acids, proteins, urea, or sodium chloride), an excipient (e.g. sugars, amino acids, urea, or sodium chloride), an antioxidant, an antiseptic, an isotonizing agent, or an buffer may also be added according to the necessity.

Such composition (b) as described above may be used as a pre-formulated product or may be prepared before use for administration to a patient. Thus, the non-specific immunopotentiator as an active ingredient of composition (b) as well as an emulsion or other preparation as the dosage form may be used as a pre-formed product in which the constituents have already been mixed together, or may be prepared before use for administration to a patient.

A method of inducing antigen-specific T cells according to the present invention which comprises administering compositions (a) and (b) as described above is characterized in that composition (b) is administered in advance and then composition (a) is administered. In particular, composition (a) is preferably administered 6 or more hours after the administration of composition (b), and more preferably composition (a) is administered 12 or more hours after the administration of composition (b). Further preferably, composition (a) is administered about 12 to 48 hours after the administration of composition (b), and still more preferably, composition (a) is administered about 24 to 48 hours after the administration of composition (b). The most preferable timing of administration is such that composition (a) is administered about 24 hours (ca. 1 day; 20 to 28 hours) after the administration of composition (b).

In this connection, administration may be carried out in any manner so long as the timing of administration is such that, as described above, composition (b) is administered in advance and then composition (a) is administered, and therefore, examples of an administration procedure include:

1) composition (b) is administered one or more times, and after a certain period as described above, composition (a) is administered; or 2) composition (b) is administered one or more times, and after a certain period as described above, compositions (b) and (a) are simultaneously administered.

In this regard, when composition (b) is administered two or more times, the number of administrations may be, in particular, 2 to 10, and preferably 2 to 5.

Taking the above administrations of (a) and (b) as one administration cycle, such an administration cycle may be repeated two or more times in order to further improve the effect on induction of T cells. Thus, the administration cycle may be repeated two or more times as appropriate depending, for example, on the disease to be treated, the symptoms, age, and weight of the patient. The interval between the repeated administration cycles may also be determined as appropriate in the range from about one week to about one year depending, for example, on the symptoms of the patient.

The route of administration for compositions (a) and (b) used in a method of inducing antigen-specific T cells according to the present invention may be, for example, intradermal administration, subcutaneous administration, continuous subcutaneous administration, intravenous injection, intraarterial injection, intramuscular injection, local infusion, or intraperitoneal administration. It is also possible to continuously and slowly administer using, for example, an osmotic pump, or to prepare a sustained-release formulation (e.g. a mini-pellet formulation) and implant it. Preferred is intradermal or subcutaneous administration. It is particularly preferred to intradermally administer both of compositions (a) and (b). In that case, it is preferred to intradermally administer compositions (a) and (b) at the same site.

Exemplary combinations of the active ingredients of the above compositions (a) and (b) in a method of inducing antigen-specific T cells according to the present invention may be combinations of an antigen protein with a bacterium-derived component or a derivative thereof, with a cytokine, with a plant-derived component or a derivative thereof, or with a marine organism-derived component or a derivative thereof, or may also be combinations of an antigen peptide with a bacterium-derived component or a derivative thereof, with a cytokine, with a plant-derived component or a derivative thereof, or with a marine organism-derived component or a derivative thereof. Among these combinations, when the antigen is a cancer antigen, preferred are a combination of a cancer antigen protein with a bacterium-derived component or a derivative thereof, or a combination of a cancer antigen peptide with a bacterium-derived component or a derivative thereof, because they enable more effective induction of antigen-specific T cells.

In this connection, a preferable bacterium-derived component is Ancer, Broncasma Berna, Krestin, or Picibanil. Likewise, in the case that the active ingredient of (b) is a cytokine, a combination of a cancer antigen protein with INF-α, or a combination of a cancer antigen peptide with IFN-α is preferred. In the case that the active ingredient of (b) is a marine organism-derived component, a combination of a cancer antigen protein or a cancer antigen peptide with α-galactosylceramide is preferred.

When the active ingredient of composition (a) is a cancer antigen protein, a specific example may be a combination of WT1 (SEQ ID NO: 1) with a bacterium-derived component or a derivative thereof, a combination of WT1 with a cytokine, a combination of WT1 with a plant-derived component or a derivative thereof, or a combination of WT1 with a marine organism-derived component or a derivative thereof. Preferred is a combination of WT1 with a bacterium-derived component or a derivative thereof, and more preferred is a combination of WT1 with Ancer, Broncasma Berna, Krestin, or Picibanil. In addition, a combination of WT1 with IFN-α, and a combination of WT1 with α-galactosylceramide are also preferable embodiments.

Likewise, when the active ingredient of composition (a) is a cancer antigen peptide, a specific example may be a combination of a cancer antigen peptide derived from WT1 with a bacterium-derived component or a derivative thereof, a combination of a cancer antigen peptide derived from WT1 with a cytokine, a combination of a cancer antigen peptide derived from WT1 with a plant-derived component or a derivative thereof, or a combination of a cancer antigen peptide derived from WT1 with a marine organism-derived component or a derivative thereof. Preferred is a combination of a cancer antigen peptide derived from WT1 with a bacterium-derived component or a derivative thereof, and more preferred is a combination of a cancer antigen peptide derived from WT1 with Ancer, Broncasma Berna, Krestin, or Picibanil.

In addition, a combination of a cancer antigen peptide derived from WT1 with IFN-α, and a combination of a cancer antigen peptide derived from WT1 with α-galactosylceramide are also preferable embodiments.

In this context, the cancer antigen peptide derived from WT1 may be those peptides found in the amino acid sequence of human WT1 set forth in SEQ ID NO: 1 which have a motif structure as described above that is bound and presented by an HLA antigen, as well as altered peptides thereof. Particular examples are the peptides listed in Table II to Table XLVI of WO 2000/18795 and altered peptides based on the motifs, and more preferable, Arg Met Phe Pro Asn Ala Pro Tyr Leu (SEQ ID NO: 2) and Cys Met Thr Trp Asn Gln Met Asn Leu (SEQ ID NO: 3) which have a binding motif for HLA-A2 and HLA-A24, or altered peptides thereof based on the HLA-A24 or HLA-A2 binding motif. A specific example of such altered peptides is Cys Tyr Thr Trp Asn Gln Met Asn Leu (SEQ ID NO: 4) in which Met at position 2 of the peptide set forth in SEQ ID NO: 3 has been replace by Tyr, an amino acid consistent with the motif.

A method of inducing antigen-specific T cells according to the present invention as described above may be examined for its ability to induce antigen-specific T cells as follows.

Composition (b) according to the present invention is injected intradermally into a laboratory animal, and after 24 hours, composition (a) is injected intradermally. Taking these administrations as one course, vaccination is conducted once or several times at intervals of one to two weeks. One week after the last administration, the spleen is removed, and lymphocytes are prepared from the spleen. Splenocytes from unprimed mice are also prepared in parallel, and pulsed with an antigen peptide for several hours followed by X-irradiation at a dose of about 2000 to 5000 rad to use as antigen-presenting cells. Lymphocytes from immunized mice are restimulated with the antigen peptide in a culture system by adding thereto the antigen-presenting cells. If necessary, similar stimulation is conducted several times at a frequency of once a week. One week after the last stimulation, lymphocytes are recovered, and may be examined for their ability to induce antigen-specific T cells using target cells such as cells pulsed with the antigen peptide or cells positive for the antigen, for example, by determining the amounts of various cytokines (e.g. IFN-γ) produced in response by antigen peptide-specific T cells induced among lymphocytes, or by measuring the cytotoxicity of antigen peptide-specific T cells against target cells labeled with $^{51}$Cr according to the $^{51}$Cr release assay (J. Immunol., 139:2888, 1987). For human, peripheral blood mononuclear cells (PBMCs) isolated from peripheral blood, for example, by the Ficoll method may be used instead of splenic lymphocytes of laboratory animals in order to examine, in a similar manner, the ability to induce antigen peptide-specific T cells.

It is also possible to examine the ability to induce cancer antigen-specific T cells by the procedures described below in the Examples. Briefly, cDNA encoding a cancer antigen protein of interest is introduced into a tumor cell to prepare tumor cells highly expressing the cancer antigen protein of interest. The tumor cells are administered intraperitoneally, and vaccination is started on the next day. Vaccination is achieved by four courses of administration conducted at intervals of one week; one course of administration consisting of first intradermally injecting composition (b) as described above, and after 24 hours, intradermally injecting composition (a). Then, anti-tumor effects based on the ability to induce antigen-specific T cells may be examined by measuring a tumorigenic rate, a survival rate, or a disease-free survival rate using a routine method. Alternatively, an administration procedure similar to that described above may be conducted on a tumor patient instead of a laboratory animal to examine the ability to induce antigen peptide-specific T cells.

When applied to an antigen-positive patient, a method of inducing antigen-specific T cells according to the present invention can cause an antigen peptide to be presented at a high density with an HLA antigen on antigen-presenting cells and can thereby induce proliferation of T cells specific for the presented HLA antigen-peptide complex, leading to killing of target cells (cells positive for the antigen peptide) or activation of immunity by production of various cytokines. A method of inducing antigen-specific T cells according to the present invention, where the antigen is a cancer antigen, is used for treatment or prevention of a cancer. In particular, it is used for treatment or prevention of, for example, lung, ovarian, and prostatic cancer as well as leukemia. Likewise, the method is used for treatment or prevention of viral infections, where the antigen is a virus-derived antigen.

In treatment or prevention of a cancer, a method of inducing antigen-specific T cells according to the present invention can induce and enhance specific cellular immunity against cancer cells, and thereby treat a cancer or prevent proliferation and metastasis of a cancer. In addition, a method of inducing antigen-specific T cells according to the present invention may be used in combination with a conventional chemotherapy or radiotherapy to enhance the therapeutic effects. In treatment or prevention of a viral infection, a method of inducing antigen-specific T cells according to the present invention can induce and enhance specific cellular immunity against virus-infected cells, and can thereby treat or prevent a virus infection.

Although the timing of starting a method of inducing antigen-specific T cells according to the present invention is not specifically limited, the method may be preferably carried out, for example, after a patient with leukemia has attained complete remission (CR), or during situations in which the number of tumor cells has been reduced by a solid cancer surgery, that is, the patient has achieved a state of minimal residual disease (MRD).

In connection with the above embodiments, the present invention provides a method of treatment and/or prevention of a cancer in a patient comprising a method for inducing antigen-specific T cells in the patient according to the present invention.

In another embodiment, the present invention relates to a pharmaceutical composition for enhancing an activity of an antigen protein or an antigen peptide to induce antigen-specific T cells, which comprises a non-specific immunopotentiator as an active ingredient, and which is administered before the administration of the antigen protein or the antigen peptide; and to a pharmaceutical composition for enhancing an anticancer activity based on the immunopotentiating action of a non-specific immunopotentiator, which comprises an antigen protein or an antigen peptide as an active ingredient and which is administered after the administration of said non-specific immunopotentiator, wherein the anticancer activity is enhanced by the activity to induce antigen-specific T cells. The compositions comprising a non-specific immunopotentiator as described above may be prepared and used according to the above descriptions for composition (b), while the compositions comprising an antigen protein or an antigen peptide as described above may be prepared and used according to the above descriptions for composition (a).

In connection with the above embodiments, the present invention provides a pharmaceutical composition of the present invention for enhancing an activity of an antigen protein or an antigen peptide to induce antigen-specific T cells, or a pharmaceutical composition of the present invention for enhancing an anticancer activity based on the immunopotentiating action of a non-specific immunopotentiator wherein the anticancer activity is enhanced by the activity to induce antigen-specific T cells, said pharmaceutical composition being for use in treatment and/or prevention of a cancer.

Furthermore, in connection with the above embodiments, the present invention provides a use of a non-specific immunopotentiator for preparing a medicament which is administered before the administration of an antigen protein or an antigen peptide and which enhances an activity of the antigen protein or the antigen peptide to induce antigen-specific T cells, as well as a use of an antigen protein or an antigen peptide for preparing a medicament which is administered after the administration of a non-specific immunopotentiator and which enhances an anticancer activity based on the immunopotentiating action of said non-specific immunopotentiator by means of the activity of the protein or the peptide to induce antigen-specific T cells. In addition, the present invention provides a use of a non-specific immunopotentiator for preparing a medicament which is administered before the administration of an antigen protein or an antigen peptide and which enhances an activity of the antigen protein or the antigen peptide to induce antigen-specific T cells and thereby treats and/or prevents a cancer, as well as a use of an antigen protein or an antigen peptide for preparing a medicament which is administered after the administration of a non-specific immunopotentiator and which enhances an anticancer activity based on the immunopotentiating action of said non-specific immunopotentiator by means of the activity to induce antigen-specific T cells and thereby treats and/or prevent a cancer. In these embodiments, the antigen protein or the antigen peptide, and the non-specific immunopotentiator may be prepared and used according to the above descriptions for compositions (a) and (b).

In particular embodiments, the present invention also provides a pharmaceutical composition for enhancing an activity of WT1 protein set forth in SEQ ID NO: 1 or a cancer antigen peptide derived from said WT1 protein to induce antigen-specific T cells, which comprises a bacterium-derived component or a derivative thereof as an active ingredient, as well as a pharmaceutical composition for enhancing an anticancer activity based on the immunopotentiating action of a bacterium-derived component or a derivative thereof, which comprises as an active ingredient WT1 protein set forth in SEQ ID NO: 1 or a cancer antigen peptide derived from said WT1 protein wherein the anticancer activity is enhanced by the activity of the protein or the peptide to induce antigen-specific T cells. The present invention also provides a pharmaceutical composition for enhancing an activity of WT1 protein set forth in SEQ ID NO: 1 or a cancer antigen peptide derived from said WT1 protein to induce antigen-specific T cells, which comprises IFN-α as an active ingredient, as well as a pharmaceutical composition for enhancing an anticancer activity based on the immunopotentiating action of IFN-α, which comprises as an active ingredient WT1 protein set forth in SEQ ID NO: 1 or a cancer antigen peptide derived from said WT1 protein wherein the anticancer activity is enhanced by the activity of the protein or the peptide to induce antigen-specific T cells. These embodiments also include a pharmaceutical composition for inducing antigen-specific T cells which comprises WT1 protein set forth in SEQ ID NO: 1 or a cancer antigen peptide derived from said WT1 protein along with a bacterium-derived component or a derivative thereof. Likewise, a pharmaceutical composition for inducing antigen-specific T cells which comprises WT1 protein set forth in SEQ ID NO: 1 or a cancer antigen peptide derived from said WT1 protein along with IFN-α is also included.

As shown in the following Examples, when used in combination with various bacterium-derived components or IFN-α, WT1 consistently produced good CTL (cytotoxic T cell)-inducing effects and thus anti-tumor effects. It is therefore expected that a therapeutic and/or prophylactic agent for cancer which employs WT1 in combination with a bacterium-derived component, or a therapeutic and/or prophylactic agent for cancer which employs WT1 in combination with IFN-α will exert clinical effects as an excellent anti-tumor-specific immunotherapeutic agent. When WT1 is used in combination with various bacterium-derived components or IFN-α, either of WT1 and bacterium-derived components or IFN-α may be administered first, or they may be mixed together before the administration.

Although the bacterium-derived component or a derivative thereof used in combination with WT1 protein is not specifically limited, preferred are a combinations of WT1 with Ancer, a combination of WT1 with Broncasma Berna, a combination of WT1 with Krestin, and a combination of WT1 with Picibanil.

Likewise, although the bacterium-derived component or a derivative thereof used in combination with a cancer antigen peptide derived from WT1 is not specifically limited, preferred are a combinations of a cancer antigen peptide derived from WT1 with Ancer, a combination of a cancer antigen peptide derived from WT1 with Broncasma Berna, a combination of a cancer antigen peptide derived from WT1 with Krestin, and a combination of a cancer antigen peptide derived from WT1 with Picibanil. In this context, the cancer antigen peptide derived from WT1 may be those peptides found in the amino acid sequence of human WT1 set forth in SEQ ID NO: 1 which have a motif structure as described above that is bound and presented by an HLA antigen, as well as altered peptides thereof. Particular examples are the peptides listed in Table II to Table XLVI of WO 2000/18795 and altered peptides based on the motifs, and more preferable, Arg Met Phe Pro Asn Ala Pro Tyr Leu (SEQ ID NO: 2) and Cys Met Thr Trp Asn Gln Met Asn Leu (SEQ ID NO: 3) which have a binding motif for HLA-A2 and HLA-A24, or altered peptides thereof based on the HLA-A24 or HLA-A2 binding motif. A specific example of such altered peptides is Cys Tyr Thr Trp Asn Gln Met Asn Leu (SEQ ID NO: 4) in which Met at position 2 of the peptide set forth in SEQ ID NO: 3 has been replace by Tyr, an amino acid consistent with the motif.

Regarding the therapeutic and/or prophylactic agent for cancer involving a combination of WT1 and a bacterium-derived component as described above, administration methods, doses, dosage forms and the like are similar to those described above for the method of inducing antigen-specific T cells.

In connection with these embodiments, the present invention relates to:

a method for enhancing, in a patient, an activity of WT1 protein set forth in SEQ ID NO: 1 or a cancer antigen peptide derived from said WT1 protein to induce antigen-specific T cells, which comprises administering to said patient a bacterium-derived component or a derivative thereof, or IFN-α in an amount effective to enhance the activity to induce antigen-specific T cells;

a method for enhancing, in a patient, an anticancer activity based on the immunopotentiating action of a bacterium-derived component or a derivative thereof, or of IFN-α, which comprises administering to said patient WT1 protein set forth in SEQ ID NO: 1 or a cancer antigen peptide derived from said WT1 protein in an amount effective to enhance the anticancer activity based on the immunopotentiating action;

the method as described above wherein the agents are administered to a cancer patient for treatment and/or prevention of a cancer; and the method as described above wherein WT1 protein set forth in SEQ ID NO: 1 or a cancer antigen peptide derived from said WT1 protein is administered at the same time with a bacterium-derived component or a derivative thereof, or with IFN-α; as well as a use of a bacterium-derived component or a derivative thereof, or of IFN-α, for preparing a medicament which enhances an activity of WT1 protein set forth in SEQ ID NO: 1 or a cancer antigen peptide derived from said WT1 protein to induce antigen-specific T cells;

a use of WT1 protein set forth in SEQ ID NO: 1 or a cancer antigen peptide derived from said WT1 protein for preparing a medicament which enhance an anticancer activity based on the immunopotentiating action of a bacterium-derived component or a derivative thereof, or of IFN-α, by means of the activity of the protein or the peptide to induce antigen-specific T cells;

the method as described above for preparing a medicament which is administered to a cancer patient for treatment and/or prevention of a cancer;

the use as described above for preparing a medicament which comprises WT1 protein set forth in SEQ ID NO: 1 or a cancer antigen peptide derived from said WT1 protein along with a bacterium-derived component or a derivative thereof or with IFN-α.

Embodiments of such a method and use as described above involving a combination of WT1 with a bacterium-derived component or IFN-α are similar to those described above for the method of inducing antigen-specific T cells.

EXAMPLES

The present invention is illustrated below by reference to the following Examples. The present invention is not, however, limited to such Examples.

Example 1

Anti-Tumor Effects of a Combination of a WT1 Peptide and Ancer

1. Materials and Methods
1) Cells
C1498, a leukemia cell line derived from a C57BL/6 mouse which does not express WT1, was purchased from ATCC (Rockville, Md.). C1498 (WT1-C1498) was prepared by transfecting C1498 cells with cDNA for mouse WT1 (WO 00/06602) in the usual manner.

2) Peptide

A 9-mer peptide which represents a cancer antigen peptide derived from WT1 (sequence: Arg Met Phe Pro Asn Ala Pro Tyr Leu; SEQ ID NO: 2) was synthesized using Fmoc chemistry on an ABI 430A peptide synthesizer (Applied Biosystems Inc., Foster), and then purified by reverse phase chromatography using a C18 Microbondasphere (Waters Japan, Osaka) column. The synthesized peptide was analyzed using an API IIIE triple quadrupole mass spectrometer (Sciex, Toronto, Canada), and the concentration of peptide was determined by MicroBCA assay (Pierce, Rockford, Ill.) using BSA as a standard.

3) Non-Specific Immunopotentiator

Ancer 20 Injection (Zeria Pharmaceutical Co.), an agent against radiotherapy-induced leukopenia which primarily comprises polysaccharides obtained from hot water extract of human *Mycobacterium tuberculosis*, was purchased and used as a non-specific immunopotentiator.

4) Mice

Male C57BL/6 mice, 6 to 8 weeks old, were purchased from CLEA Japan, Inc.

5) Schedule for Tumor Cell Transplantation and Vaccination

Into mice, 1×10⁶ WT1-C1498 cells were injected intraperitoneally, and vaccination was started on the next day. Into flanks of the mice, 0.2 ml of Ancer 20 Injection was injected intradermally, and after 24 hours, 0.1 ml of a 2 mg/ml WT1 peptide (SEQ ID NO: 2) solution was injected intradermally at the same site. Taking these administrations as one course, four courses of vaccination were conducted in total, at intervals of one week (FIG. 1). Five mice were used per group.

2. Results

Figure 2:
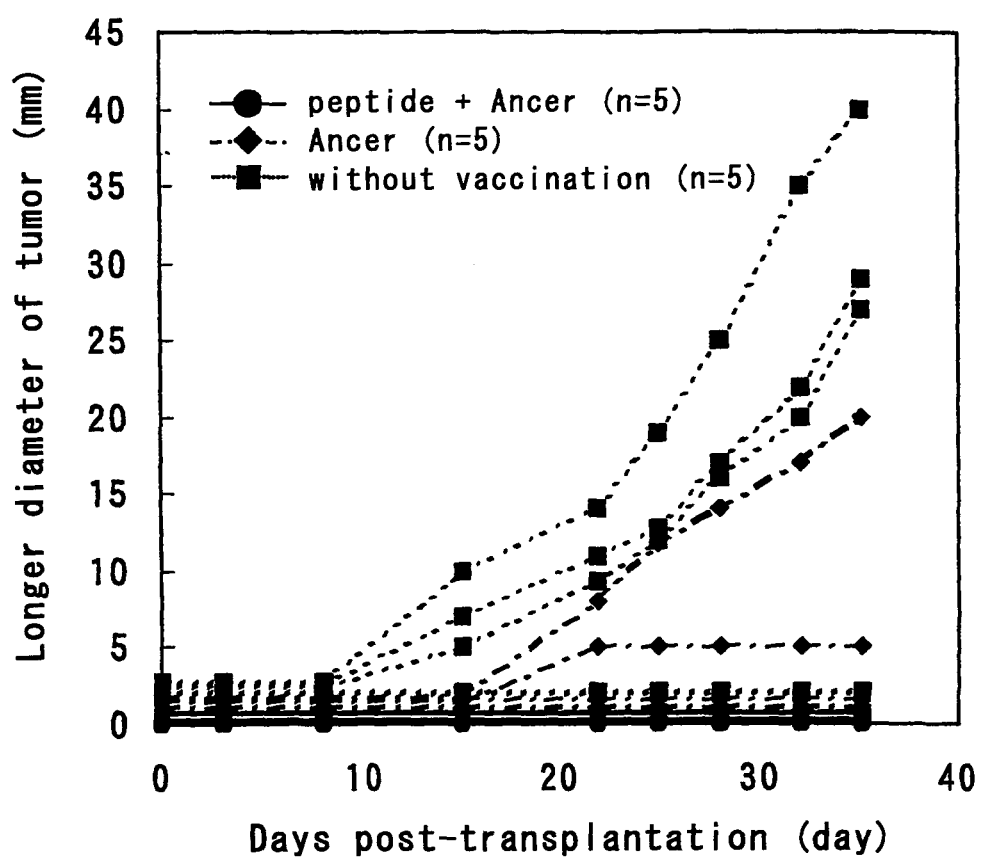
FIG. 2 is a graph showing the longer diameters of tumors in mm up until Day 35 after transplantation of tumor cells in experiments using a WT1 peptide and Ancer. In the figure, solid circles indicate results of WT1 peptide+Ancer administration, solid diamonds indicate results of Ancer administration, and solid squares indicate results without any vaccination.

According to the schedule shown in FIG. 1, tumor cell transplantation and vaccine administration were conducted, and the subsequent formation of tumor masses was observed. FIG. 2 shows the tumor diameters in the mice observed in the experiments using Ancer as a non-specific immunopotentiator. In the group without any vaccination, rapid formation of tumor masses was observed in 3 out of 5 mice. In the group receiving Ancer alone, although formation of tumor masses was observed in 2 out of 5 mice, the rate of tumor mass formation was slower and the tumor diameter was smaller as compared to those observed in the mice in the group without any vaccination which exhibited tumor mass formation. In the group received the WT1 peptide and Ancer, none of the 5 mice exhibited formation of tumor masses.

These results demonstrated that although administration of the non-specific immunopotentiator alone exerted a weak inhibitory effect on tumor growth, a combination of the non-specific immunopotentiator with the WT1 peptide resulted in more potent anti-tumor effects.

Example 2

Anti-Tumor Effects of a Combination of a WT1 Peptide and Broncasma Berna

1. Materials and Methods

1) Cells, Peptide, and Mice

Prepared as describe in Example 1.

2) Non-Specific Immunopotentiator

Broncasma Berna (Sanwa Kagaku Kenkyusho Co.), an immunotherapeutic agent for upper respiratory allergies which is a mixed dead microbial suspension obtained from various bacteria, was purchased and used as a non-specific immunopotentiator.

3) Schedule for Tumor Cell Transplantation and Vaccination

Into mice, 1×10⁶ WT1-C1498 cells were injected intraperitoneally, and vaccination was started on the next day. Into flanks of the mice, 0.5 ml of Broncasma Berna was injected intradermally, and after 24 hours, 0.1 ml of a 2 mg/ml WT1 peptide (SEQ ID NO: 2) solution was injected intradermally at the same site. Taking these administrations as one course, four courses of vaccination were conducted in total, at intervals of one week (FIG. 1). Five mice were used per group.

2. Results

Figure 3:
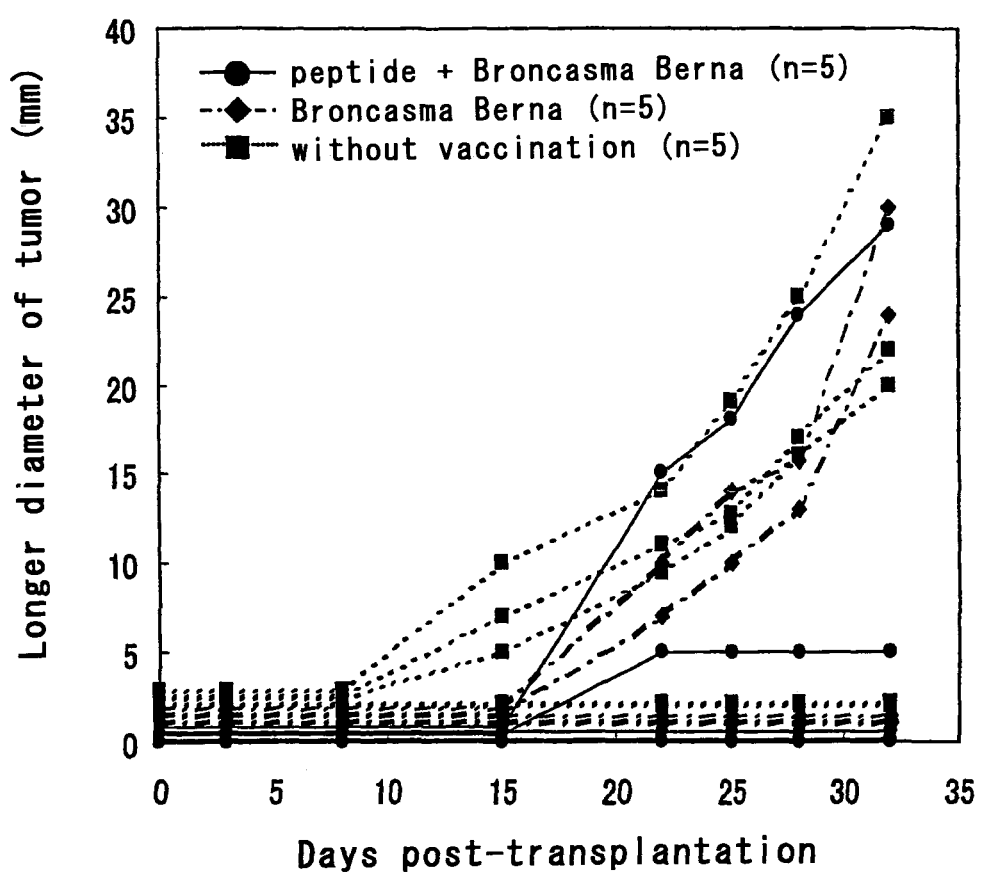
FIG. 3 is a graph showing the longer diameters of tumors in mm up until Day 32 after transplantation of tumor cells in experiments using a WT1 peptide and Broncasma Berna. In the figure, solid circles indicate results of WT1 peptide+Broncasma Berna administration, solid diamonds indicate results of Broncasma Berna administration, and solid squares indicate results without any vaccination.

According to the schedule shown in FIG. 1, tumor cell transplantation and vaccine administration were conducted, and the subsequent formation of tumor masses was observed. FIG. 3 shows the tumor diameters in the mice observed in the experiments using Broncasma Berna as a non-specific immunopotentiator. In the group without any vaccination, rapid formation of tumor masses was observed in 3 out of 5 mice. In the group receiving Broncasma Berna alone, rapid formation of tumor masses was observed in 2 out of 5 mice, and the tumor diameters 35 days after tumor transplantation were more than 25 mm in both cases. In the group received the WT1 peptide and Broncasma Berna, although formation of tumor masses was observed in 1 out of 5 mice, no formation of tumor masses was observed at all in 3 out of remaining 4 mice, and in one mouse, tumor formation was obviously inhibited to 5 mm or below.

These results demonstrated that although administration of the non-specific immunopotentiator alone exerted a weak inhibitory effect on tumor growth, a combination of the non-specific immunopotentiator with the WT1 peptide resulted in more potent anti-tumor effects.

Example 3

Effect of a Combination of a WT1 Peptide and Picibanil on Induction of Antigen Peptide-Specific CTLs 1. Materials and Methods 1) Peptide A 9-mer peptide which is an HLA-A24-restricted antigen peptide derivative derived from human WT1 (sequence: Cys Tyr Thr Trp Asn Gln Met Asn Leu; SEQ ID NO: 4) was synthesized using Fmoc chemistry.

2) Non-Specific Immunopotentiator

Picibanil (Chugai Pharmaceuticals Co.), an anti-tumor agent derived from hemolytic streptococci, was purchased and used as a non-specific immunopotentiator. On the day of administration, 5 KE/vial of Picibanil was suspended in 0.5 ml of physiological saline to prepare a 10 KE/ml solution.

3) Mice

A transgenic mouse into which a chimeric gene consisting of α1 and α2 domains derived from human HLA-A2402 and of remaining regions derived from mouse $K^b$ (sometimes referred to as HLA-A2402/$K^b$) has been introduced were produced and used in the experiments. The transgenic mouse was produced as follows. An HLA-A2402 genomic DNA fragment was amplified by PCR from genomic DNA of a human tumor cell line RERF-LC-AI (RIKEN Cell Bank, RCB0444). The primers used were an upstream primer containing a restriction site for Hind III: 5'-CGC AGG CTC TCA CAC TAT TCA GGT GAT CTC-3' (SEQ ID NO: 5) and a down stream primer containing a restriction site for Bgl II: 5'-CGG GAG ATC TAC AGG CGA TCA GGT AGG CGC-3' (SEQ ID NO: 61. The amplified fragment containing the genetic regions for promoter, α1, and α2 of HLA-A2402 was ligated into a phagemid vector pBluescript (Stratagene) at the Hind III and the Bam HI cleavage sites to obtain a plasmid encoding HLA-A2402 genetic regions necessary for construction of the chimeric gene. A genomic DNA fragment of H-2K$^b$ was amplified by PCR from genomic DNA of a mouse tumor cell line EL-4 (ATCC TIB-39). The primers used were an upstream primer: 5'-CGC AGG CTC TCA CAC TAT TCA GGT GAT CTC-3' (SEQ ID NO: 7) and a downstream primer containing an Eco RI restriction site added thereto: 5'-CGG AAT TCC GAG TCT CTG ATC TTT AGC CCT GGG GGC TC-3' (SEQ ID NO: 8). The amplified fragment was ligated into a phagemid vector pBluescript at the Kpn I and the Eco RI cleavage sites to obtain a plasmid encoding the α3, transmembrane, and cytoplasmic regions of H-2K$^b$ gene necessary for construction of the chimeric gene. The plasmid encoding HLA-A2402 genomic DNA as described above was cleaved at the site for the restriction enzyme Bgl II, while the H-2K$^b$ gene as described above was cleaved at the site for the restriction enzyme Bam HI, and these sites were then ligated to each other to prepared the chimeric gene between HLA-A2402 and H-2K$^b$, that is, HLA-A2402/K$^b$. HLA-A2402/K$^b$ was introduced into a fertilized egg from a C57BL/6 mouse to produce a transgenic mouse expressing HLA-A2402.

4) Schedule for Vaccination and Measurement of CTL Activity

On Day 0, 2 KE of Picibanil was injected intradermally into mice at their flanks, and on the next day, 0.1 ml of a 2 mg/ml WT1 peptide (SEQ ID NO: 4) solution was injected intradermally at the same sites. Three mice were used. On Day 8, the spleen was removed, disrupted by grinding them on the frosted part of a slide glass, and the red blood cells were lysed in ACK buffer (0.15 M NH$_4$Cl, 10 mM KHCO$_3$, 0.1 mM EDTA, pH 7.2-7.4) to recover and prepare the splenocytes. A portion of the splenocytes was X-irradiated (2,000 rad), pulsed for one hour with the above peptide at 100 μg/ml, and plated onto a 24-well plate at a density of 0.7×10$^6$ cells/well. During this procedure, non-irradiated and non-peptide-pulsed splenocytes were simultaneously added at a density of 7×10$^6$ cells/well to re-stimulate them at 37° C. (the final concentration of the peptide: 1 μg/ml). Splenocytes were cultured separately for each individual. For cultivation, 10 ml of culture medium (CTM culture medium) comprising RPMI 1640 medium supplemented with 10% FCS, 10 mM HEPES, 20 mM L-glutamine, 1 mM sodium pyruvate, 1 mM MEM nonessential amino acids, 1% MEM vitamins, 55 μM 2-mercaptoethanol was used, and the in vitro stimulation was continued for 5 days. On the other hand, Jurkat-A2402/K$^b$ cells, cells from a human tumor cell line Jurkat (ATCC TIB-152) into which the above HLA-A2402/K$^b$ gene has been stably introduced, were labeled with 3.7 MBq/10$^6$ cells of $^{51}$Cr, and then pulsed for one hour with the above peptide at 100 μg/ml (labeling was continued for 2 hours, and one hour after initiation of the labeling, the peptide was added at a final concentration of 100 μg/ml). In addition, non-peptide-pulsed cells were also prepared as control target cells. The Jurkat-A2402/K$^b$ thus prepared was used as target cells to which the peptide-restimulated splenocytes from transgenic mice were added. The CTL activity was then measured by the $^{51}$Cr release assay (J. Immunol., 159:4753, 1997). The cell number ratio of splenocytes to target cells was 60:1.

2. Results

Figure 4:
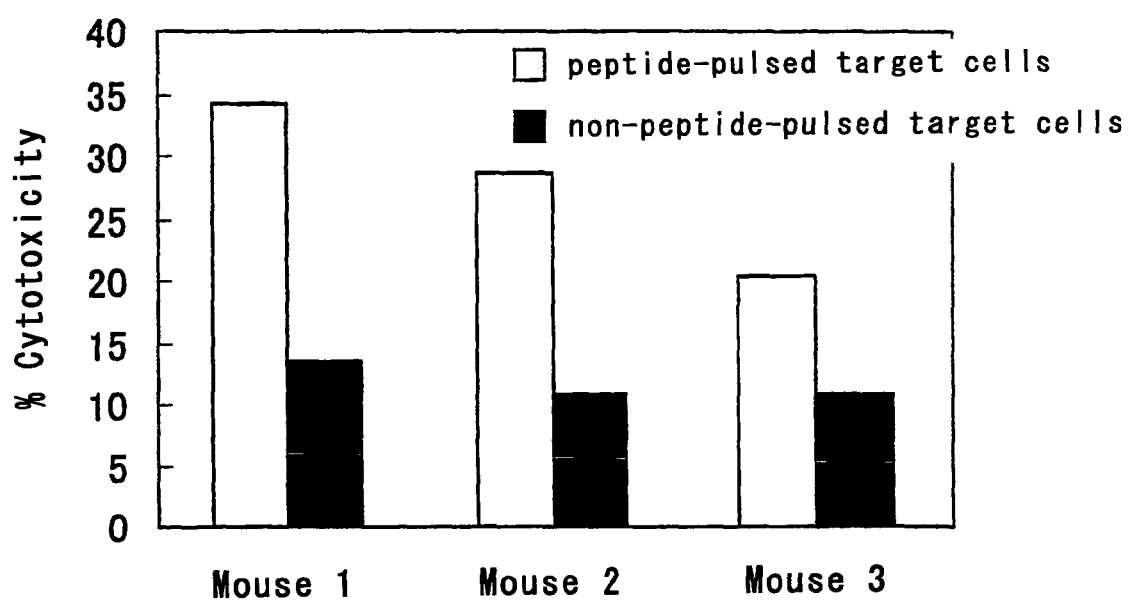
FIG. 4 is a graph showing the antigen peptide-specific CTL-inducing effect of WT1 peptide and Picibanil administration.

FIG. 4 shows the CTL activities in the three vaccinated mice. The splenocytes from the three mice exhibited greater cytotoxic activities against target cells pulsed with the antigen peptide, when compared to those against target cells not pulsed with the antigen peptide. These results demonstrated that the vaccination method in which Picibanil is first administered intradermally and on the next day a WT1 peptide solution is administered intradermally at the same site efficiently induced peptide-specific CTLs.

Example 4

Effect of a Combination of a WT1 Peptide and IFN-α on Induction of Antigen Peptide-Specific CTLs 1. Materials and Methods 1) Peptide and mice Prepared as described in Example 3.

2) Non-Specific Immunopotentiator

Mouse IFN-α was used as a non-specific immunopotentiator. A mouse cell line EAT cells (derived from Ehrlich's ascites carcinoma; ATCC CCL-77) pre-treated with sodium acetate were infected with Newcastle disease virus, treated with theophylline, and allowed to produce IFN-α, which was then purified on a CPG column and an anti-IFN-α antibody column.

3) Schedule for Vaccination and Measurement of CTL Activity

On Day 0, 200 μl of IFN-α (corresponding to 5×10$^4$ U) was, injected intradermally into mice at their flanks, and on the next day, 0.1 ml of a 2 mg/ml WT1 peptide (SEQ ID NO: 4) solution was injected intradermally at the same sites. Three mice were used. On Day 8 or later, peptide-restimulation was conducted and activity of antigen peptide-specific CTLs was measured, as described for the above Example, except that the splenocytes for restimulation were prepared using combined splenocytes obtained from three mice.

2. Results

Figure 5:
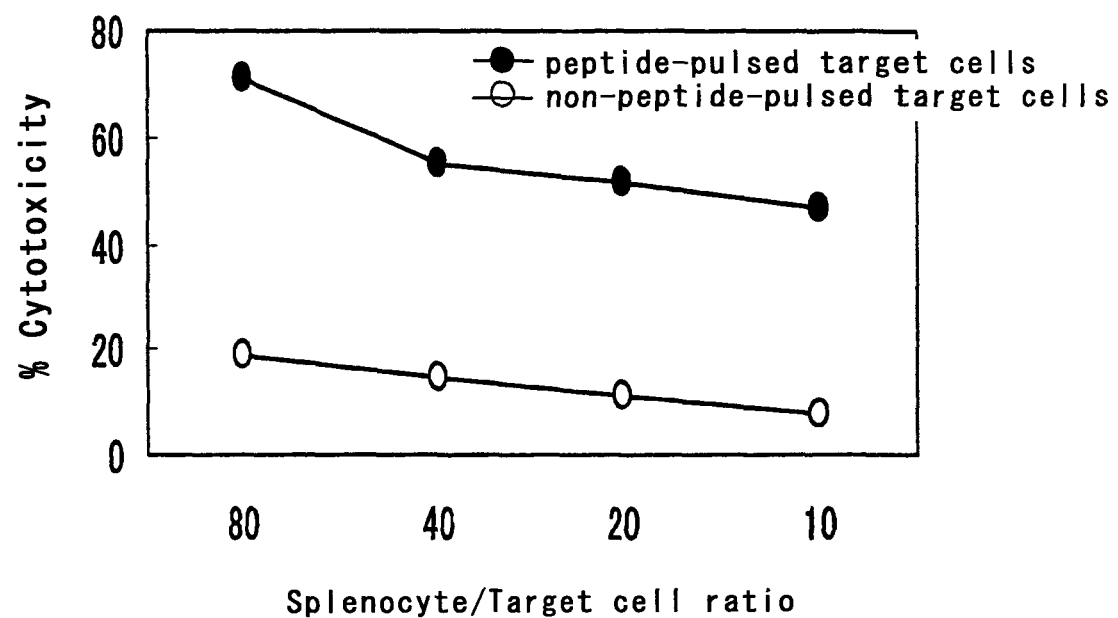
FIG. 5 is a graph showing the antigen peptide-specific CTL-inducing effect of WT1 peptide and IFN-α administration.

FIG. 5 shows the results. The splenocytes exhibited greater cytotoxic activities against target cells pulsed with the antigen peptide, as compared to those against target cells not pulsed with the antigen peptide. These results demonstrated that the vaccination method in which IFN-α is first administered intradermally and on the next day a WT1 peptide solution is administered intradermally at the same site efficiently induced peptide-specific CTLs.

Example 5

Anti-Tumor Effects of a Combination of a WT1 Peptide and Krestin

1. Materials and Methods

1) Cells

3LL cells, a lung cancer cell line derived from a C57/BL6 mouse, were transfected in the usual manner with a cDNA for mouse WT1, and WT1-3LL cells thereby obtained were used.

2) Peptide

Prepared as described in Example 1.

3) Non-Specific Immunopotentiator

Krestin (Sankyo Co.), an anti-tumor agent comprising a basidiomycete-derived polysaccharide, was purchased and used as a non-specific immunopotentiator.

4) Transplantation of Tumor Cells and Schedule for Vaccination Into mice, 5×10$^4$ WT1-3LL cells were injected subcutaneously, and vaccination was started on the next day. Into flanks of the mice, 100 μg of Krestin was injected intradermally, and after 24 hours, 0.1 ml of a 2 mg/ml WT1 peptide (SEQ ID NO: 2) solution was injected intradermally at the same site. Taking these administrations as one course, three courses of vaccination were conducted in total, at intervals of one week.

2. Results

Figure 6:
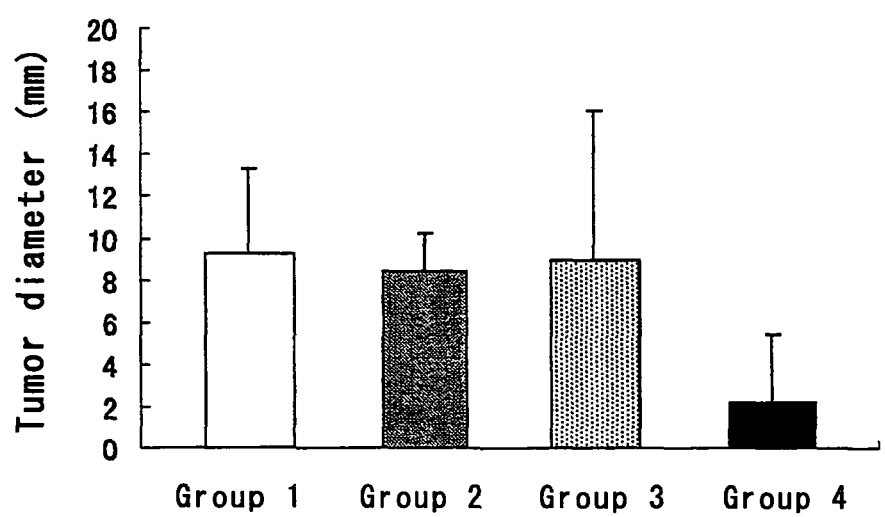
FIG. 6 is a graph showing the mean diameters of tumors in mm on Day 18 after transplantation of tumor cells. Group 1 represents a group without any vaccination; Group 2 represents a group received a WT1 peptide alone; Group 3 represents received Krestin alone; and Group4 represents a group received Krestin and the WT1 peptide. In the figure, bars depicted on the columns indicate standard deviations for each group.

FIG. 6 shows the tumor diameters measured on Day 18 after 3 courses of vaccine administration have been completed, taking the day of tumor cell transplantation as Day 0. In the group received Krestin and the WT1 peptide, engraftment of tumor cells was not observed in 3 out of 5 mice. On the contrary, in the group without any vaccination (5 mice), the group received the peptide alone (5 mice), and the group received Krestin alone (4 mice), engraftment of tumor cells was observed in all cases, and the average values were greater than that of the group received Krestin and the WT1 peptide. Student's t-test conducted between the unvaccinated group and other groups reveled a significant difference (p<0.05) only in the group received Krestin and the WT1 peptide.

These results demonstrated that a combination of the non-specific immunotherapeutic agent with the WT1 peptide resulted in more potent anti-tumor effects.

INDUSTRIAL APPLICABILITY

The method of the present invention enables efficient induction of antigen-specific T cells. The method of inducing antigen-specific T cells and related pharmaceutical compositions according to the present invention can efficiently, simply and conveniently induce antigen-specific T cells, and are thus useful as anticancer or antiviral agents.

---

The invention claimed is:

1. A method for inducing antigen-specific T cells in a patient in need thereof, comprising administering intradermally at the same site to the patient a composition (a) which comprises a therapeutically effective amount of a peptide fragment consisting of Arg Met Phe Pro Asn Ala Pro Tyr Leu (SEQ ID NO: 2) or Cys Tyr Thr Trp Asn Gln Met Asn Leu (SEQ ID NO: 4) as an active ingredient and a composition (b) which comprises a therapeutically effective amount of IFN-α as an active ingredient,
    wherein the composition (b) is administered to the patient about 24 hours prior to administering the composition (a).

2. A method according to claim 1, wherein the administration of the composition (a) and the composition (b) is repeated two or more times.

3. A method of treatment of a cancer in a patient, which comprises a method according to claim 1.

4. The method of claim 1, wherein the patient has cancer.

5. The method of claim 1, wherein the peptide fragment consists of SEQ ID NO: 2.

6. The method of claim 1, wherein the peptide fragment consists of SEQ ID NO: 4.

* * * * *

SEQUENCE LISTING

<160> NUMBER OF SEQ ID NOS: 8

<210> SEQ ID NO 1
<211> LENGTH: 449
<212> TYPE: PRT
<213> ORGANISM: Homo sapiens

<400> SEQUENCE: 1

```
Met Gly Ser Asp Val Arg Asp Leu Asn Ala Leu Leu Pro Ala Val Pro
  1               5                  10                  15

Ser Leu Gly Gly Gly Gly Gly Cys Ala Leu Pro Val Ser Gly Ala Ala
                 20                  25                  30

Gln Trp Ala Pro Val Leu Asp Phe Ala Pro Pro Gly Ala Ser Ala Tyr
             35                  40                  45

Gly Ser Leu Gly Gly Pro Ala Pro Pro Ala Pro Pro Pro Pro
         50                  55                  60

Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270
```

```
Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
        290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
                355                 360                 365

Gln Leu Lys Arg His Gln Arg Arg His Thr Gly Val Lys Pro Phe Gln
            370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
                420                 425                 430

Arg His His Asn Met His Gln Arg Asn Met Thr Lys Leu Gln Leu Ala
            435                 440                 445

Leu

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Arg Met Phe Pro Asn Ala Pro Tyr Leu

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Cys Met Thr Trp Asn Gln Met Asn Leu

<210> SEQ ID NO 4
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 4

Cys Tyr Thr Trp Asn Gln Met Asn Leu

<210> SEQ ID NO 5
<211> LENGTH: 30
<212> TYPE: DNA
<213> ORGANISM: Artificial Sequence
<220> FEATURE:
<223> OTHER INFORMATION: Upstream primer containing a restriction site
      for Hind III
```

-continued

```
<400> SEQUENCE: 5
cgcaggctct cacactattc aggtgatctc                                     30

<210> SEQ ID NO 6
<211> LENGTH: 30
<212> TYPE: DNA
<213> ORGANISM: Artificial Sequence
<220> FEATURE:
<223> OTHER INFORMATION: Downstream primer containing a restriction site
      for Bgl II

<400> SEQUENCE: 6
cgggagatct acaggcgatc aggtaggcgc                                     30

<210> SEQ ID NO 7
<211> LENGTH: 30
<212> TYPE: DNA
<213> ORGANISM: Artificial Sequence
<220> FEATURE:
<223> OTHER INFORMATION: Upstream primer used in the PCR amplification
      of a genomic DNA fragment of H-2Kb

<400> SEQUENCE: 7
cgcaggctct cacactattc aggtgatctc                                     30

<210> SEQ ID NO 8
<211> LENGTH: 38
<212> TYPE: DNA
<213> ORGANISM: Artificial Sequence
<220> FEATURE:
<223> OTHER INFORMATION: Downstream primer containing an Eco RI
      restriction site added thereto used in the PCR amplification of a
      genomic DNA fragment of H-2Kb

<400> SEQUENCE: 8
cggaattccg agtctctgat ctttagccct gggggctc                            38
```